United States Patent [19]
Aoki et al.

[11] Patent Number: 5,121,320
[45] Date of Patent: Jun. 9, 1992

[54] SYSTEM FOR READING AND DISPLAYING AN EDIT-PROCESSED DNA PATTERN

[75] Inventors: Yoshiaki Aoki; Toshitsugu Okayama, both of Yokohama, Japan

[73] Assignee: Hitachi Software Engineering Co., Ltd., Yokohama, Japan

[21] Appl. No.: 422,578

[22] Filed: Oct. 17, 1989

[30] Foreign Application Priority Data

Oct. 17, 1988 [JP] Japan ................ 63-261036

[51] Int. Cl.$^5$ .............. G06F 15/00; G06K 9/00
[52] U.S. Cl. .................... 364/413.01; 382/6
[58] Field of Search ............. 364/413.01; 382/6

[56] References Cited

U.S. PATENT DOCUMENTS

| | | | |
|---|---|---|---|
| 4,706,192 | 11/1987 | Nasu et al. | 364/413.01 |
| 4,720,786 | 1/1988 | Hara | 364/413.01 |
| 4,802,101 | 1/1989 | Hara | 364/413.01 X |
| 4,837,687 | 6/1989 | Tanaka et al. | 364/413.01 |
| 4,837,733 | 6/1989 | Shiraishi et al. | 364/413.01 X |
| 4,862,360 | 8/1989 | Kimura et al. | 364/413.01 |
| 4,941,092 | 7/1990 | Hara et al. | 364/413.01 X |
| 4,982,326 | 1/1991 | Kaneko | 364/413.01 |

Primary Examiner—Dale M. Shaw
Assistant Examiner—Xuong M. Chung
Attorney, Agent, or Firm—Fay, Sharpe, Beall, Fagan, Minnich & McKee

[57] ABSTRACT

The edit processing includes band deletion processing and band addition processing for correcting the DNA pattern image. Additionally, a concentration graph display indicative of a distribution of concentration of the DNA pattern is provided.

8 Claims, 20 Drawing Sheets

FIG. 7A

CONTENT OF FILM IMAGE DATA

| START POSTN FOR OBTNG IMAGE DATA (sp) | END POSTN FOR OBTNG IMAGE DATA (ep) | NUMBER OF DATA OBTND IN THE y-DIRECTN PER LANE (yl) |
|---|---|---|
| IMAGE ON LOWEST PORTN x-DIRECTN SEGMNTD IMAGE DATA PER LANE (CONC VALUES FROM 0 TO 255) | | |
| --- | | |
| IMAGE ON UPPERMOST PORTN x-DIRECTN DATA PER LANE | | |

Top brace: $sp - ep + 1$

Right brace: $yl \times 4$

FIG. 7B

CONTENT OF DNA SEQ RECOGNTN DATA

| DNA CODES (A/C/G/T) | y-COORDINATE DEVIATN BETWN 2ND LANE CENTR AXIS/NORMALIZN AXIS | COORDINATES OF NORMALIZD POSTN | y-COORDINATE DEVIATN BETWN 4TH LANE CENTR AXIS/NORMALIZN AXIS | ENTRY OF TOP SEQ |
|---|---|---|---|---|
| y-COORDINATE DEVIATN BETWN 1ST LANE CENTR AXIS/NORMALIZN AXIS | | y-COORDINATE DEVIATN BETWN 3RD LANE CENTR AXIS/NORMALIZN AXIS | | |
| y-COORDINATE DEVIATN BETWN RIGHT & LEFT ENDS OF 1ST LANE | y-COORDINATE DEVIATN BETWN RIGHT & LEFT ENDS OF 2ND LANE | y-COORDINATE DEVIATN BETWN RIGHT & LEFT ENDS OF 3RD LANE | y-COORDINATE DEVIATN BETWN RIGHT & LEFT ENDS OF 4TH LANE | |
| REPETITN BY NUMBER OF SEQ | | | | |
| | | | | ENTRY OF LAST SEQ |

SMILG DATA

FIG. 16A
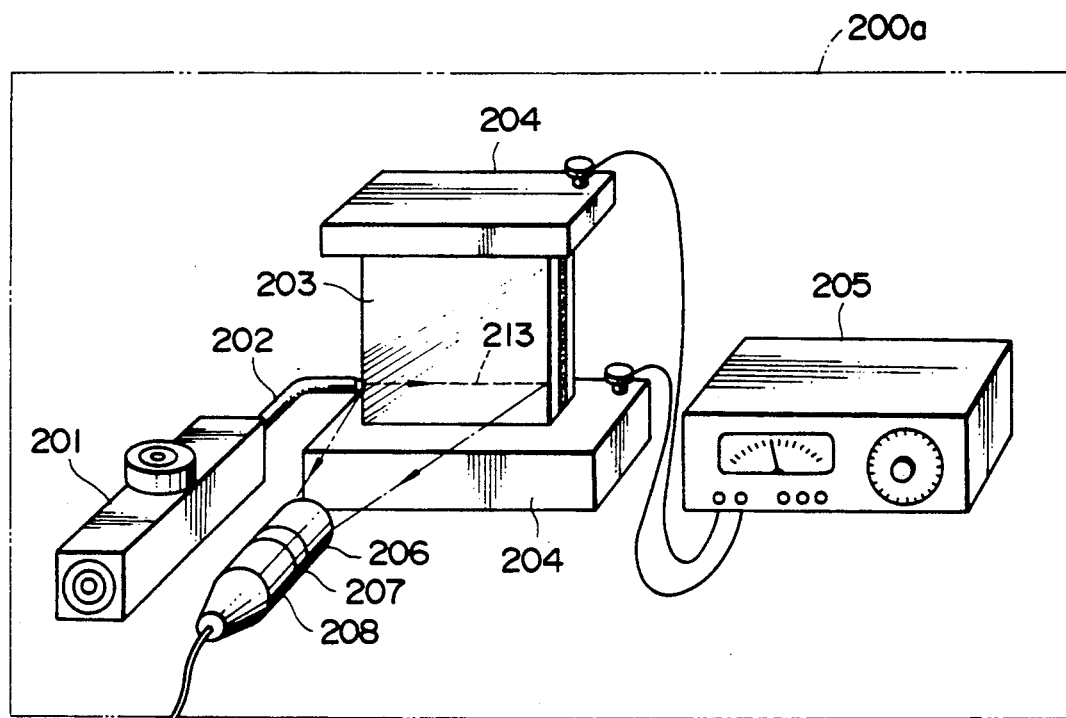
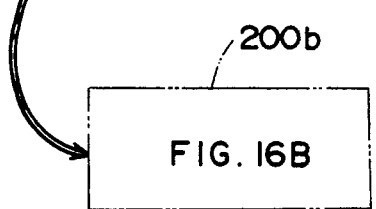
FIG. 16B

SYSTEM FOR READING AND DISPLAYING AN EDIT-PROCESSED DNA PATTERN

BACKGROUND OF THE INVENTION

The present invention relates to a DNA pattern reading apparatus and, more particularly, to a DNA pattern reading apparatus capable of subjecting a DNA fragment labelled with a radioactive isotope, a fluorescent substance or the like to electrophoresis, reading a resulting DNA pattern image as a result of electrophoresis, and automatically determining a base sequence of a gene, in which the resulting DNA pattern image is read and stored, and the stored DNA pattern image is processed, thereby permitting an accurate reading of the DNA pattern.

Heretofore, a device for determining a DNA base sequence of a gene from a DNA pattern image as a result of electrophoresis of a DNA fragment labelled with a radioactive isotope, a fluorescent substance or the like merely displays on a printer or on a display screen the base sequence determined by reading the DNA pattern by symbols A (adenine), C (cytosine), G (guanine), and T (thymine). This device is such that, if there is an error in a read result, such an error is corrected, for instance, as shown in FIG. 22, by tracing silhouettes of a band 20e of an image of bases on a DNA film as a read object, as indicated on each of base lanes 20a, 20b, 20c, and 20d, by the radioactive isotope or the like, in the direction opposite to the direction of electrophoresis and editing a DNA sequence 22.

In other words, in a DNA pattern reading device for reading the DNA film on which the DNA pattern image resulting from electrophoresis is recorded, as shown in FIG. 23, the DNA pattern reading device 21 reads the DNA film, determines its base sequence, and outputs the DNA sequence 22 as a file, and its content is merely displayed as a text on a printer 23 or on a display screen 24.

Accordingly, the DNA pattern reading device 21 suffers the disadvantage that an analyst of a base sequence should follow again the DNA pattern image of the DNA film 20 upon editing and correct an omission from the DNA sequence 22 judged or an error therein. Although a large portion of the DNA pattern reading device 21 is automatically operable, a correction of an omission or an unreadable portion of the electrophoresis pattern requires laborious work like in the case where the DNA sequence 22 is manually inputted and analyzed.

SUMMARY OF THE INVENTION

The present invention has the object to provide a DNA pattern reading apparatus capable of processing and editing a DNA pattern image of a read image, thereby reducing labor required for editing a read result of the DNA film obtained by electrophoresis.

In order to achieve the object, the present invention consists of a DNA pattern reading apparatus capable of reading a DNA pattern image resulting from electrophoresis of a labelled DNA fragment of a gene and determining a base sequence of the gene automatically, comprising an image storage for storing a read DNA pattern image, a display unit for displaying the DNA pattern image and the resulting DNA sequence on its screen, and an image recognizing and editing processing unit for judging the DNA sequence read from the DNA pattern image stored in the image storage, displaying a DNA sequence resulting from judgment, image-displaying the judged DNA pattern image and an image of each portion of the judgment process corresponding to a displayed portion of the DNA sequence as a judgment result, as well as image-processing of the DNA pattern image and the DNA sequence and editing the DNA sequence.

The image recognizing and editing processing unit comprises a concentration graph display processing unit for displaying on a screen a concentration graph indicating a distribution of concentrations in a main scan direction and in a sub scan direction of reading the DNA pattern image; a band deletion processing unit and a band addition processing unit for modifying the DNA pattern image to be judged; a smiling cursor display processing unit for forming a reference line for modifying a judgment of a distortion of the DNA pattern image; as well as a cursor transfer processing unit and a display screen scroll processing unit for implementing a screen edit processing; in which the DNA pattern image and the DNA sequence are processed and the DNA sequence is edited.

This arrangement enables a display of a text of the DNA sequence data judged by displaying a line display indicating each of bands judged so as to overlap with an image display of the DNA pattern image data displayed on a screen of the display unit and with the display of the concentration graph and by judging and editing the DNA sequence. If there would be an omission from the judgment of the DNA sequence, the DNA pattern image and the DNA sequence are subjected to an image processing and edit processing by adding or deleting data of the DNA sequence at a band position in the DNA pattern image or at the position judged in error. This edit processing can be executed by specifying a screen position to be edited by transfer of a cursor and by displaying a total DNA pattern image in the order by switching display screens consecutively by the display screen scroll processing.

This system can read the DNA pattern image recorded on the DNA film in multiple gradients and display it on the screen of the display unit in multiple gradients, thereby editing the DNA sequence. More specifically, concentrations of each of pixels consisting of the DNA pattern image are video displayed in substitution of a display in gradation, thereby permitting the DNA sequence to be edited.

As the video output of a personal computer is a video output of a digital RGB or an analog RGB in approximately two gradients, the resolution ability of the display screen is not sufficient, even if the DNA pattern is displayed as it is, for a band having a small difference of concentrations to be judged visually on the display screen. Accordingly, one pixel of the DNA film image may be displayed, for example, in four gradients using a 2×2 tile pattern, thereby raising the display resolution ability. However, a scanner to be used for the DNA pattern reading apparatus is provided with a resolution ability of approximately 256 gradients and deterioration of an image cannot be avoided in displaying a film image on the display screen even if a tile pattern would be used. In order to compete with this, the DNA pattern reading apparatus according to the present invention can display on its screen the DNA pattern image and, at the same time, display a graph of concentrations of the DNA pattern in the cross section in parallel to the center line of each of the lanes on the DNA film. As the display screen connected to a usual personal computer has a resolution ability of approximately 400 dots in the vertical direction, the concentrations of bands on each lane can be displayed in approximately 100 gradients by allocating one gradient for one dot in the vertical direction of a screen and by of four lanes on the DNA film would be disposed so as not to cause overlapping in a spaced relationship. As there is usually a difference in at least from 3 to 4 gradients out of 256 gradients between a band position and its background on the DNA film, the band position can be determined to a sufficiently accurate extent.

As has been described hereinabove, the resolution ability of a band judgment can be raised by simultaneously displaying the DNA pattern image of the DNA film read on the display screen using a tile pattern in a size of 2×2 or more, together with the concentration graph of concentrations in the lane direction of the DNA pattern image. The band display of the DNA pattern image is implemented so as to overlap with a line display indicating a band which has already been judged. The DNA pattern reading apparatus according to the present invention is further provided with functions of implementing addition processing and deletion processing of a DNA sequence at a band position at which an omission has been found as a result of a band judgment or at a position at which the judgment is made in error while the DNA pattern image and the concentration graph are being displayed. On top of that, a screen scroll is carried out so as to enable an edit processing of the DNA pattern image of a whole DNA film on a display screen. These features allow the operator to judge the DNA pattern image and confirm the resulting DNA sequence as well as correct the editing, if necessary, merely by looking at the display screen, thereby reducing a great amount of labor which has otherwise been required to edit the DNA sequence and at the same time improving accuracy in editing the read result to a remarkably high extent.

BRIEF DESCRIPTION OF THE DRAWINGS

Other objects, features and advantages of the present invention will become apparent in the course of the description of the preferred embodiments which follow, with reference to the accompanying drawings.

FIGS. 7A and 7B represent formats for the contents of the film image data and a recognition data of the DNA sequence, respectively.

FIGS. 16A and 16B are block diagrams each showing an outline of a fluorescence detection type electrophoresis capable of directly obtaining a DNA pattern image as an object to be processed in accordance with the present invention;

DESCRIPTION OF THE PREFERRED EMBODIMENTS

Figure 1:
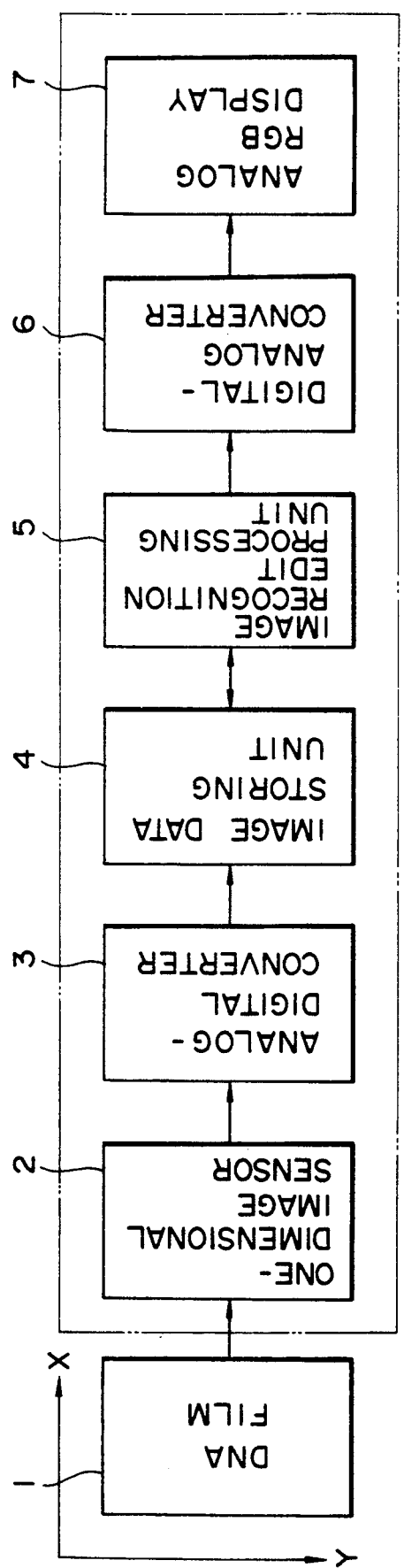
FIG. 1 is a block diagram showing an outline of a DNA pattern reading apparatus according to one example of the present invention.

Referring to FIG. 1 showing an outline of the DNA pattern reading apparatus according to the present invention, the DNA pattern reading apparatus comprises a one-dimensional image sensor 2 for reading a DNA pattern image by scanning a DNA film 1, an analog-digital (A/D) converter 3 for converting an analog signal outputted from the one-dimensional image sensor 2 into a digital signal, an image data storing unit 4 for storing data of each pixel of the DNA pattern image, an image recognition and edit processing unit 5 for determining a DNA sequence of a base sequence by reading data of the DNA pattern image from the image data storing unit 4, displaying the result, as well as correction processing and edit processing of the DNA sequence as a judgment result, a digital-analog (D/A) converter 6 for conversion into an analog signal to display image data as a result of edit processing on a display screen, and an analog RGB display 7.

An overall operation of the DNA pattern reading apparatus will be briefly described hereinafter. As shown in FIG. 1, the DNA pattern image of the DNA film 1 is scanned in the x-axial direction as a main scan direction and in the y-axial direction as a sub scan direction, and the one-dimensional image sensor 2 reads each line in the x-axial direction. Image data of the DNA pattern image read by the one-dimensional image sensor 2 is converted from an analog value to a digital value in the analog-digital converter 3 for each pixel. In this case, a concentration of one pixel is converted into an 8-bit digital value read in 256 gradients. The image data for one line portion converted into the digital value is inputted and stored in the image data storing unit 4. The DNA pattern image on a whole DNA film is continuously read in the manner as has been described hereinabove and converted into digital values followed by storage in the image data storing unit 4. The image recognition and edit processing unit 5 determines each of band positions and its gradient as well as a DNA sequence on the basis of the image data of the digitized DNA pattern image, and outputs data of the DNA sequence, together with the image data itself, into each of a plurality of files. The image recognition and edit processing unit 5 also converts the image data into a tile pattern in a one pixel unit, edits the DNA film image (DNA pattern image), and converts data of the edited DNA film image from a digital signal to an analog signal by means of the digital-analog (D/A) converter 6 followed by displays on an analog RGB display 7. At the same time, a concentration graph at the center line of each lane of the DNA pattern image is displayed. The image recognition and edit processing unit 5 simultaneously implements a line display of a judgment reference wherein smiling is taken into consideration in the band that has already been judged on the basis of data of the band positions and the gradients. At this time, a text display of the DNA sequence data is implemented simultaneously (see an example of a display screen in FIG. 15). Furthermore, the image recognition and edit processing unit 5 is provided with functions for accepting a request by the operator for a deletion from or an addition to the DNA sequence at an arbitrary position on the DNA film image and on the concentration graph and executes editing. The operator thus enables editing to correct an error in the DNA sequence while confirming the DNA sequence on the display screen.

Figure 2:
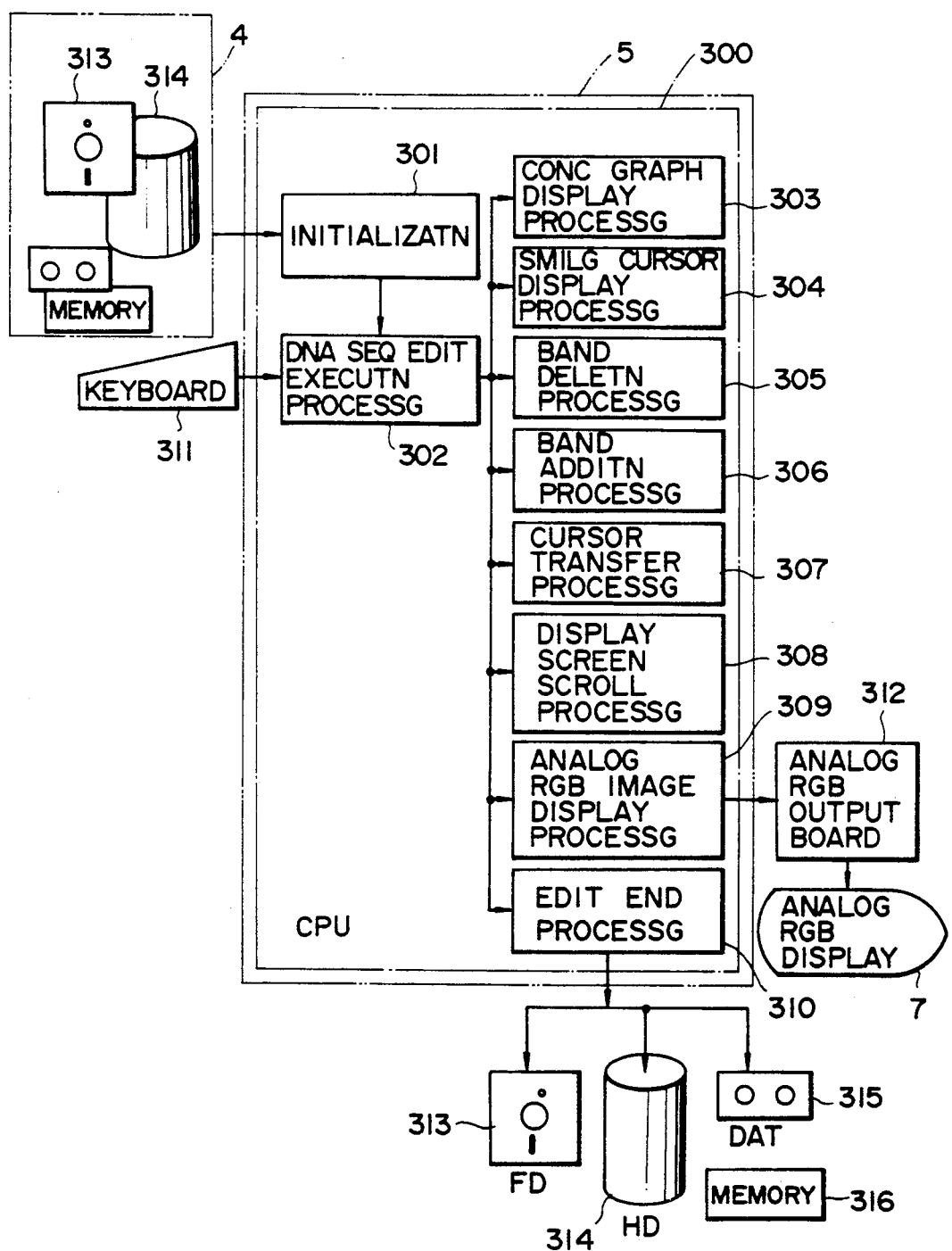
FIG. 2 is a block diagram showing an essential structure of an image recognition and edit processing unit for edit processing as a result of a DNA sequence.

A description will be made hereinafter of the edit processing of the DNA sequence using each processing routine provided in the image recognition and edit processing unit 5. FIG. 2 is a block diagram showing the structure of an essential portion of the image recognition and edit processing unit which judges and edits the DNA sequence. As shown in FIG. 2, reference numeral 300 denotes a central processing unit corresponding to the image recognition and edit processing unit 5 of FIG. 1. The central processing unit 300 for implementing each processing routine in the image recognition and edit processing unit 5 is provided with processing mechanism for processings, including an initialization processing routine 301, DNA sequence edit execution processing routine 302, concentration graph display processing routine 303, smiling cursor display processing 304, band deletion processing routine 305, band addition processing routine scroll processing routine 308, analog RGB image display routine 307, display screen processing routine 309, and edit end processing routine 310. To the central processing unit 300 for realizing the processing mechanism provided in the image recognition and edit processing unit 5 are connected an input key board 311 for giving an instruction to confirm the read result of the DNA pattern and inputting commands and so on. Keyboard 311 also operates the edit processing and the analog RGB display 7 for displaying the DNA film image as an output device, through an analog RGB output board 312 for displaying the DNA film image. An output of the edit end processing 310 is recorded in the image data storing unit 4, such as a floppy disk device (FD) 313, a hard disk device (HD) 314, a digital-audio tape device (DAT) 315, memory 316 or the like.

Figure 3:
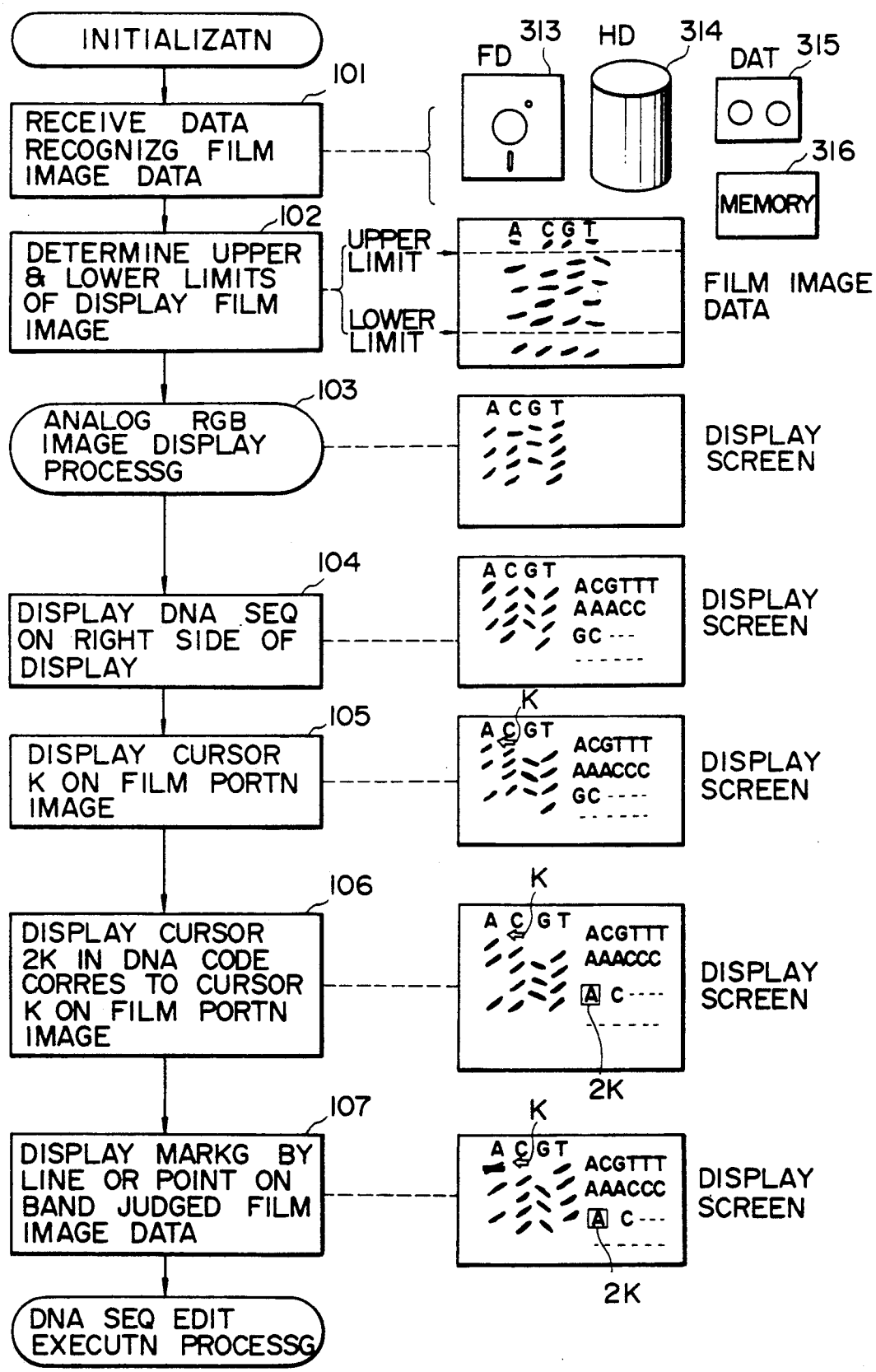
FIG. 3 is a flow chart showing a procedure of a initial processing in an image recognition and edit processing unit.

FIG. 3 is a flow chart showing the procedure of the initialization processing routine 301. As shown in FIG. 3, at step 101, film image data and recognition data stored in a recording medium including the image data storing unit 4, such as the floppy disk (FD) 313, hard disk (HD) 314, digital-analog tape (DAT) 315 or the like are supplied. Then at step 102, upper and lower bounds of the film image (DNA pattern image) to be displayed on one screen of the analog RGB display 7 are determined and, at step 103, the analog RGB image display processing is executed, thereby displaying a proportional image of the DNA pattern image on the display screen of the analog RGB display 7. Then at step 104, text data of the DNA sequence which has already been judged is displayed on the right-hand side of the display screen of the analog RGB display 7 and, at step 105, a first cursor K is displayed on the film portion image of the DNA pattern image. The flow then proceeds to step 106 where a second cursor 2K is displayed on he DNA code text of the DNA sequence corresponding to the first cursor K positioned on the film portion image. Then at step 107, a band 11 which is confirmed to have already been judged is displayed to be marked with a line 11a and transferred to the processing which follows, i.e., the DNA sequence edit execution processing.

Figure 4:
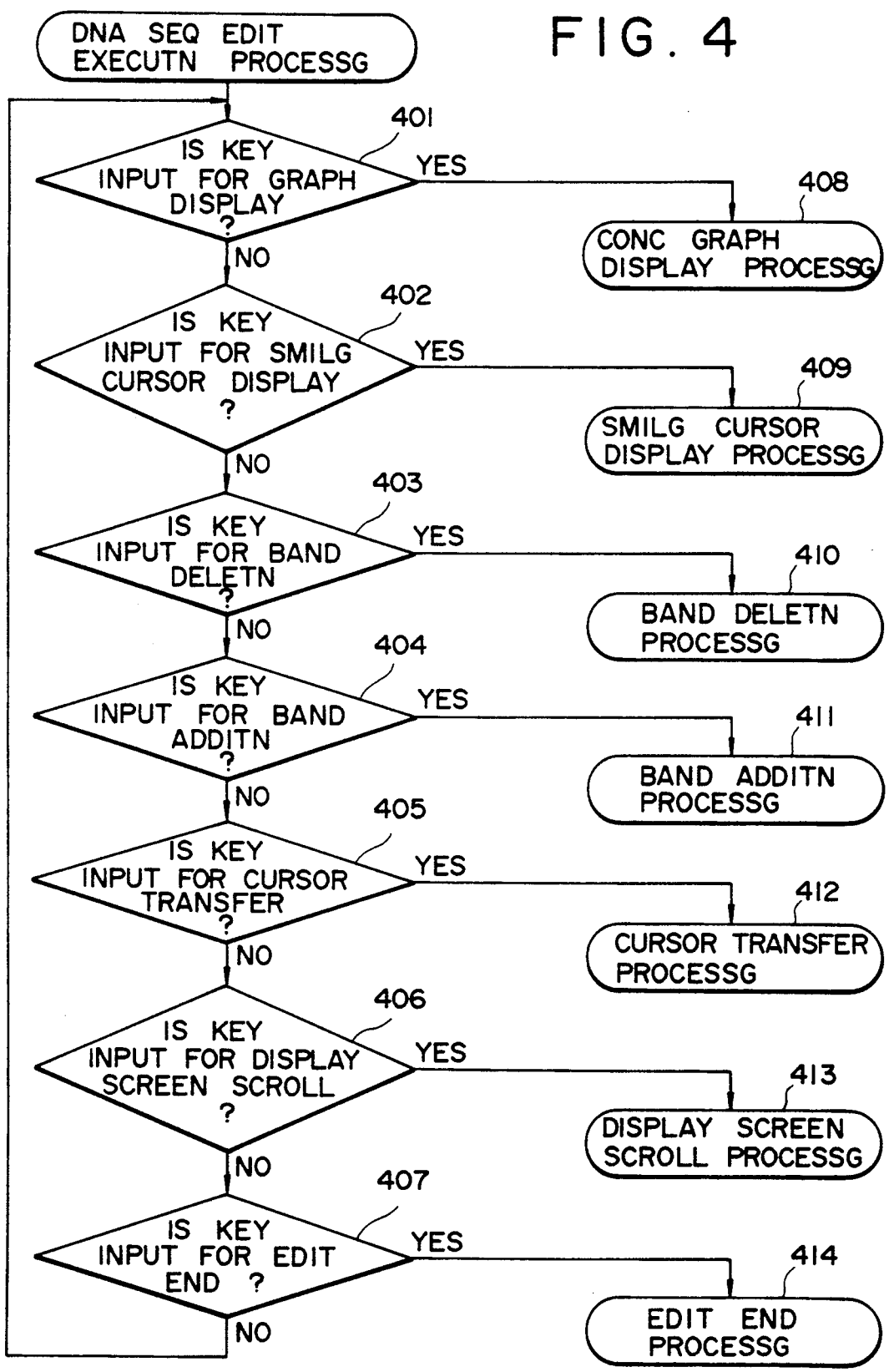
FIG. 4 is a flow chart showing a procedure of a DNA sequence edit execution processing in the image recognition and edit processing unit.

FIG. 4 is a flow chart showing the procedure of the DNA sequence edit execution processing 302. As shown in FIG. 4, the DNA sequence edit execution processing routine 302 judges commands of the key input from the keyboard 311 (FIG. 2) to execute each of the processings.

At step 401, it is judged whether or not the key input is for the command of the graph display. If YES, the flow proceeds for the concentration graph display processing 408. If NO, the step goes to step 402.

Then at step 402, whether the key input is for the command of the smiling cursor display is judged. If YES, the processing is moved for the smiling cursor display processing 409. If NO, the flow proceeds to step 403.

At step 403, it is judged whether the key input is for the command of the band deletion or not. If YES, the processing is transferred to the band deletion processing 410. If NO, the flow advances to step 404.

Step 404 is to judge whether or not the key input is for the command of the band addition. If YES, the processing is moved for the band addition processing 411. If NO, the flow goes to step 405.

At step 405, it is judged whether or not the key input is for the command of the cursor transfer processing. If YES, the flow proceeds to the cursor transfer processing 412 to move a cursor position on the film image display screen or on the DNA sequence display screen. If NO, the flow advances to step 406.

Then at step 406, whether the key input is for the command of the display screen scroll processing or not is judged. If YES, the processing is moved for the display screen scroll processing 413 where the scroll processing on the display screen is implemented. If NO, the flow goes to step 407.

At step 407, it is judged whether or not the key input is for the command of the edit end processing. If YES, the flow proceeds to the edit end processing 414 where the edit end processing is executed to update data of the DNA sequence as a result of the edit processing. If NO, the flow advances to step 401 for repeating the judgment of the key input.

Figure 5:
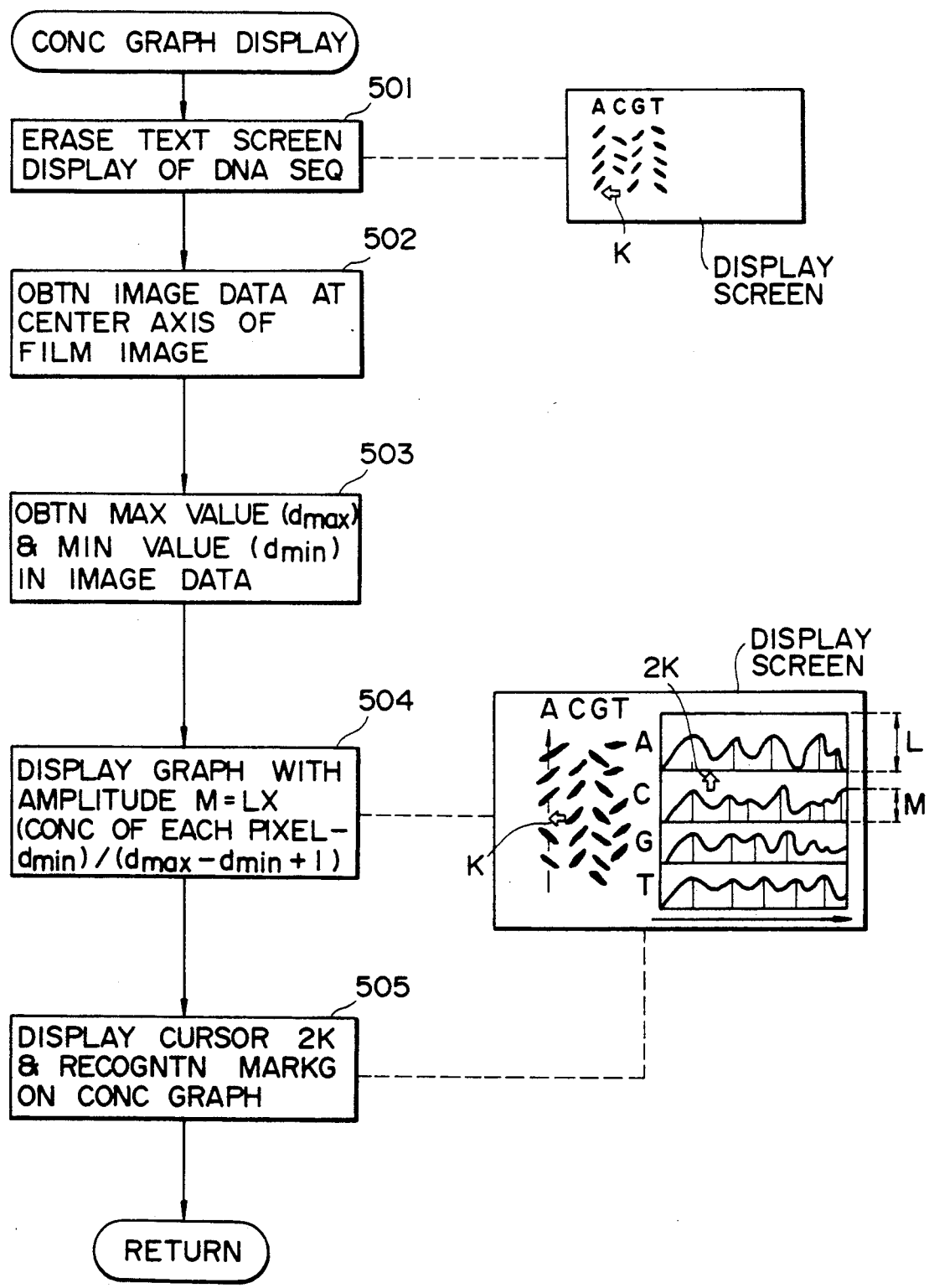
FIG. 5 is a flow chart showing a procedure of a concentration graph display processing in the image recognition and edit processing unit.

FIG. 5 is a flow chart showing the procedure of the concentration graph display processing routine 303. As shown in FIG. 5, at step 501, a text screen display of the DNA sequence is erased and, at step 502, image data of each pixel on the center axis of each lane of the film image (DNA pattern image) is obtained. Then at step 503, there are obtained the maximum value ($d_{max}$) and the minimum value ($d_{min}$) in the image data of the film image currently on display. The flow advances to step 504 where the graph is displayed with an amplitude $$M = (display\ range\ per\ lane\ L) \times (concentration\ of\ each\ pixel\ -d_{min})/(d_{max}-d_{min}+1)$$

Then at step 505, the cursor 2K and a recognition marking (display of a band which has already been judged) are displayed on the concentration graph display screen. Thereafter, the concentration graph display processing is returned.

Figure 6:
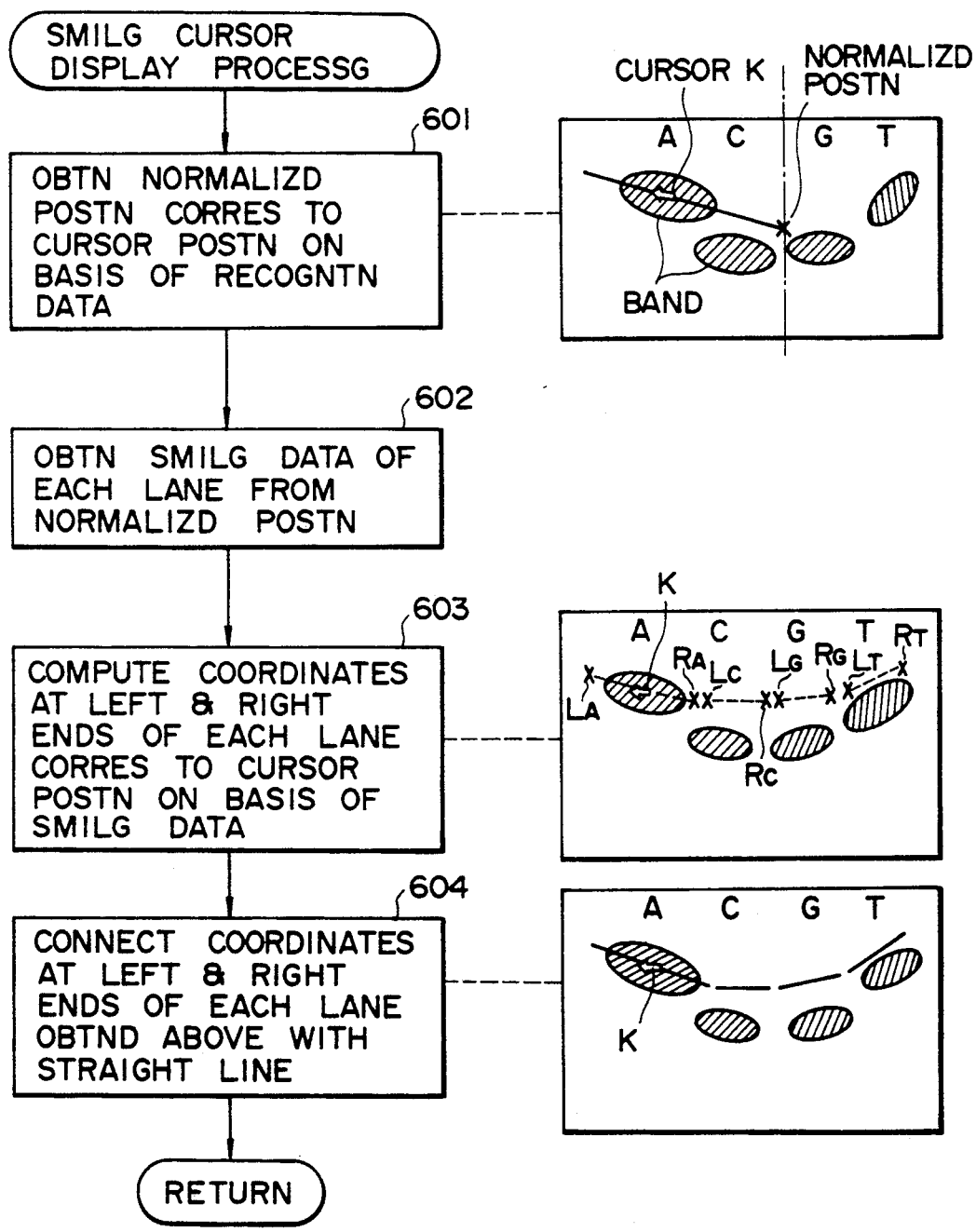
FIG. 6 is a flow chart showing a procedure of a smiling cursor display processing in the image recognition and edit processing unit.
Figure 8:
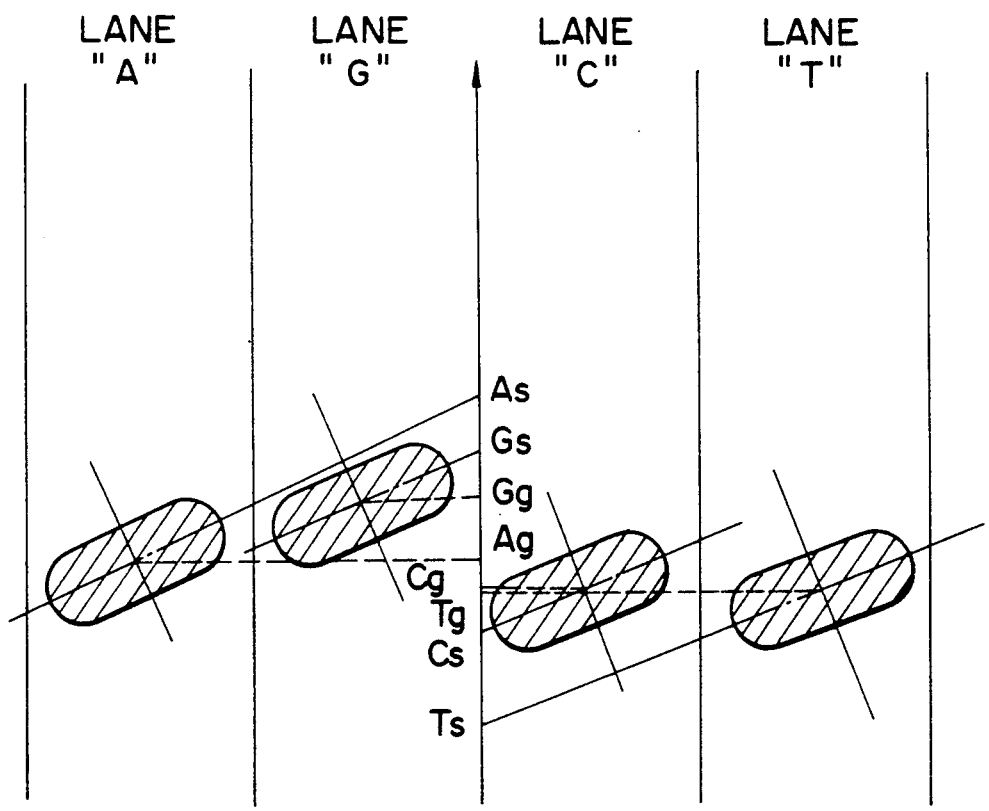
FIG. 8 represents a principle of normalization processing to be executed for central axes of four lanes.

FIG. 6 is a flow chart showing the procedure of the smiling cursor display processing routine 304. FIG. 7A represents a format for the content of film image (DNA pattern image) data, and FIG. 7B represents a format for the content of the recognition data of the DNA sequence. FIG. 8 represents a principle of the normalization processing to be executed by the center axis of the four lanes.

Referring to FIGS. 6, 7A, 7B, and 8, the smiling cursor display processing routine is described. The smiling cursor display processing routine is to form and display a smiling cursor which serves as a reference to judgment in order to judge a band without undergoing an influence of a smiling effect. As shown in FIG. 6, at step 601, there is obtained a normalized position corresponding to the cursor position on the basis of the content of the recognition data of the DNA sequence shown in FIG. 7B. The normalized position referred to herein means a position at which the band is located after the coordinate has been converted from the center axis of each of the lanes to the center axis of the four lanes. A judgment of the DNA sequence by the normalized position permits a determination of the band without any influence of the smiling effect. More specifically, as shown in FIG. 8, when the DNA sequence of bands of each lane is determined from the DNA pattern image in which each of the bands is inclined obliquely due to the smiling effect, the DNA sequence is determined by the gravitational positions (Ag, Gg, Cg, Tg) of bands to be TCAG, however, the correct DNA sequence is TCGA. Thus, in order to determine the correct DNA sequence, each of the bands is extended in the direction in which the band extends and the normalized positions (As, Gs, Cs, Ts) of the intersect ions of the extensions with the center axis 12 are given, thereby determining the correct DNA sequence. The determination of the DNA sequence by the normalized positions provides the correct DNA sequence as TCGA.

At step 602 (FIG. 6), a smiling data of each lane is obtained on the basis of the normalized positions obtained at step 601 and, at step 603, there are computed coordinates of the left-hand ends ($L_A$, $L_C$, $L_G$, $L_T$) and the right-hand ends $R_A$, $R_C$, $R_G$, $R_T$) of each of the lanes corresponding to the cursor positions on the basis of the smiling data. Then the flow proceeds to step 604 where the left-hand ends of each lane and the right-hand ends thereof obtained at step 603 are connected to each other with straight lines and the straight lines are displayed. Then the smiling cursor display processing is returned.

Figure 9:
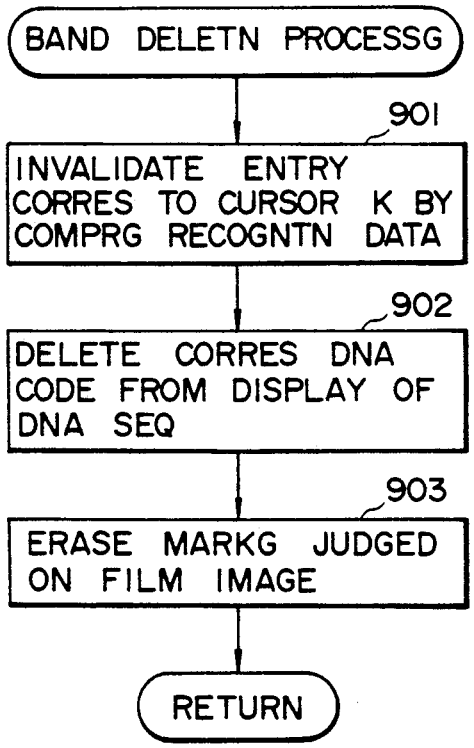
FIG. 9 is a flow chart showing a procedure of band deletion processing in the image recognition and edit processing unit.

FIG. 9 is a flow chart showing the procedure of the band deletion processing routine 305. As shown in FIG. 9, the band deletion processing routine is executed by invalidating an entry corresponding to the cursor K on the film image display on the basis of the content of the recognition data of the DNA sequence as shown in FIG. 7B at step 901, deleting the corresponding DNA code from the display of the DNA sequence at step 902, and erasing such a marking as having been judged on the film image (DNA pattern image) at step 903. Then the band deletion processing is returned.

Figure 10:
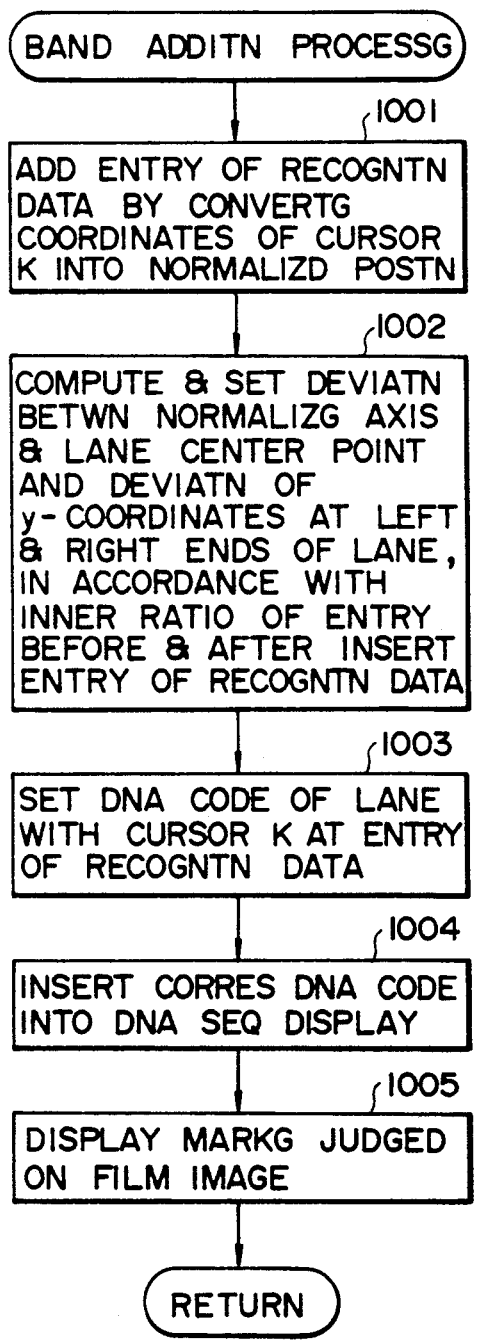
FIG. 10 is a flow chart showing a procedure of band addition processing in the image recognition and edit processing unit.

FIG. 10 is a flow chart showing the procedure of the band addition processing routine 306. As shown in FIG. 10, the band addition processing routine is implemented as follows. First at step 1001, coordinates (a band position to be added) of the cursor K are converted into its normalized positions on the basis of the content of the recognition data of the DNA sequence as shown in FIG. 7B and they are added to and inserted into the recognition data as an entry of the DNA sequence. Then at step 1002, a deviation in the y-coordinate between the normalizing axis and the center point of the lane and a deviation in the y-coordinate between the right-hand and left-hand ends of the band display are computed and set in accordance with an inner ratio of an entry (coordinates of the band position) prior to the entry (coordinates of the band position) added to and inserted into the content of the recognition data to an entry (coordinates of the band position) subsequent thereto. The flow then proceeds to step 1003, and the DNA code of the lane at which the cursor K is located is set at an entry of the recognition code. Then at step 1004, the DNA code is inserted at the position corresponding to the DNA sequence display and, at step 1005, the marking display is carried out on the screen of the film image (DNA pattern image) as having already been judged. The band addition processing is returned thereafter.

Figure 11:
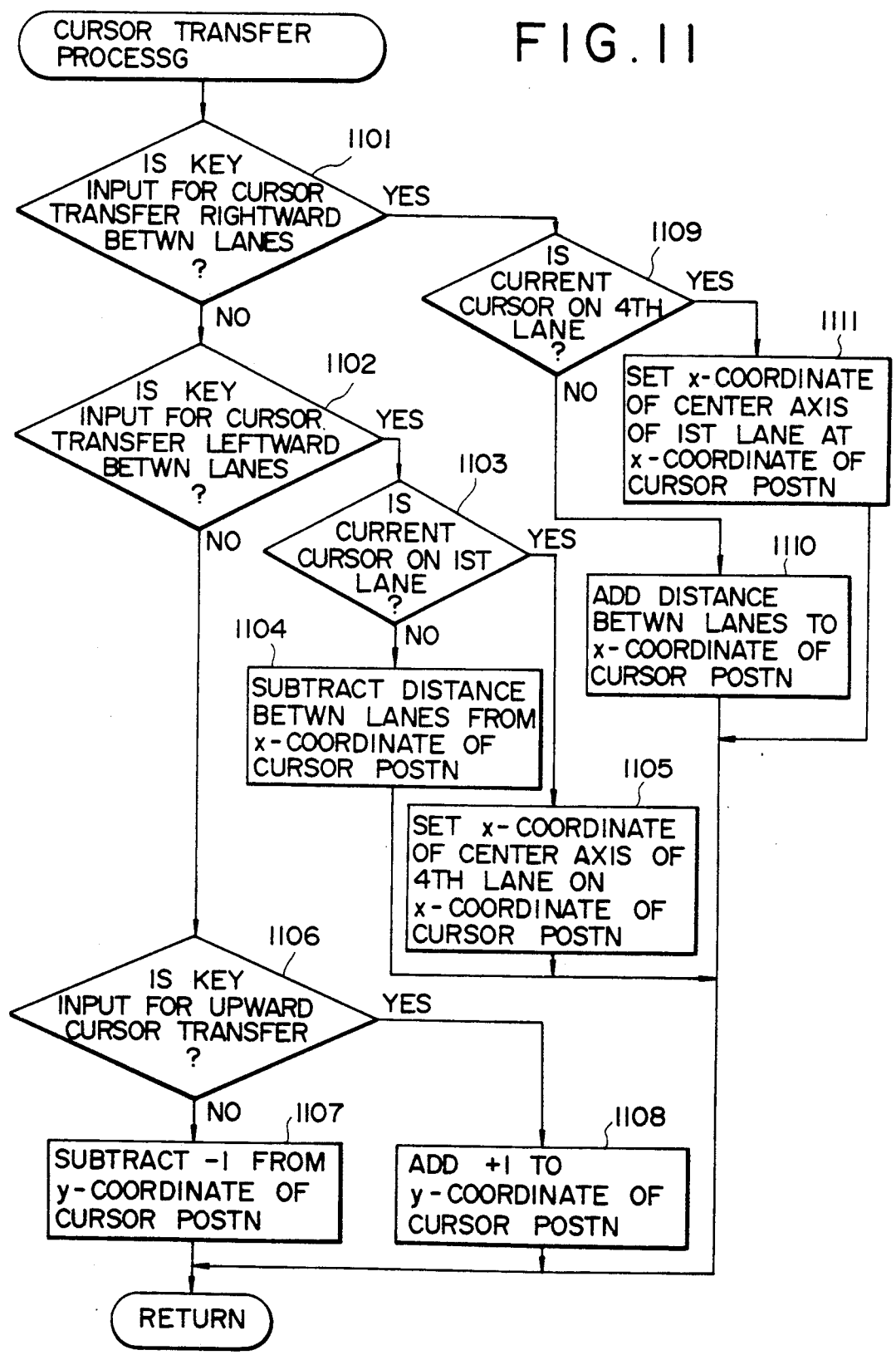
FIG. 11 is a flow chart showing a procedure of cursor transfer processing in the image recognition and edit processing unit.

FIG. 11 is a flow chart, showing the procedure of the cursor transfer processing routine 307. As shown in FIG. 11, the cursor transfer processing routine is implemented by judging the key input as to whether to require a transfer of the key to the right between lanes at step 1101 and transferring the key to step 1109 if the judgment at step 1101 is YES or transferring the key to step 1102 if the judgment at step 1101 is NO. In step 1109, it is judged whether or not the current cursor position is located on the fourth lane. If YES, the flow proceeds to step 1111 to set the x-coordinate of the center axis of the first lane at the x-coordinate of the cursor position. If the judgment at step 1109 is NO, the flow goes to step 1110 where a distance between the lanes is added to the x-coordinate of the cursor position.

At step 1102, it is judged whether or not the key input is for a request of a transfer of the cursor to the left between the lanes. If YES, the flow proceeds to step 1103, and if NO, the flow proceeds to step 1106. At step 1103, it is judged whether or not the current cursor position is on the first lane. If YES at step 1103, the flow advances to step 1105 where the x-coordinate of the center axis of the fourth lane is set at the x-coordinate of the current cursor position. If this judgment at step 1103 is NO, the flow goes to step 1104 where a distance between the lanes is subtracted from the x-coordinate of the current cursor position.

At step 1106, it is judged whether or not the key input is for a request for an upward transfer of the cursor. If YES, the flow goes to step 1108 and "1" is added (+1) to the y-coordinate of the current cursor position. If NO, the flow proceeds to step 1107 where "1" is subtracted (−1) from the y-coordinate of the current cursor position. Thereafter, the cursor transfer processing is returned.

Figure 12:
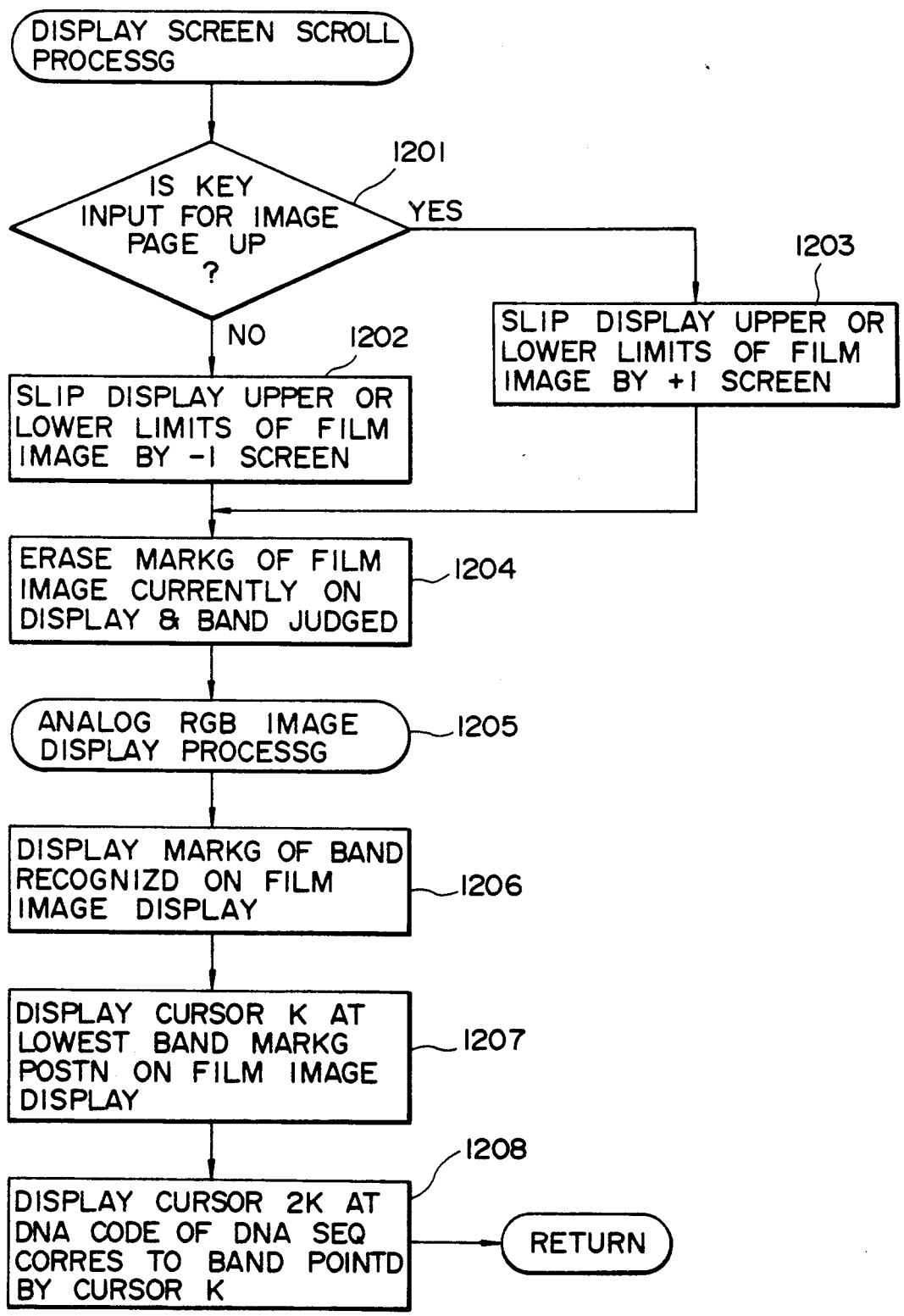
FIG. 12 is a flow chart showing a procedure of display screen scroll processing in the image recognition and edit processing unit.

FIG. 12 is a flow chart showing the procedure of the display screen scroll processing routine 308. As shown in FIG. 12, the display screen scroll processing routine is implemented. First, at step 1201, it is judged whether or not the key input is for a request for image page up. If YES, the flow proceeds to step 1203 where the upper bound or the lower bound of the film image display is slipped by a one (+1) screen portion. If NO, the flow goes to step 1202 and the upper bound or the lower bound of the film image display is slipped by a one (−1) screen portion. Then at step 1204, the film image currently on display and the marking of the band which has already been recognized are erased. At step 1205, an analog RGB of the portion image of the film image is displayed and, at step 1206, the marking of the judged band is displayed on the film image display. Then at step 1207, the cursor K is displayed at the lowest band marking position on the film image display and, at step 1208, the cursor 2K is displayed on the DNA code of the DNA sequence corresponding to the band pointed by the cursor K. Thereafter the display screen scroll processing is returned.

Figure 13:
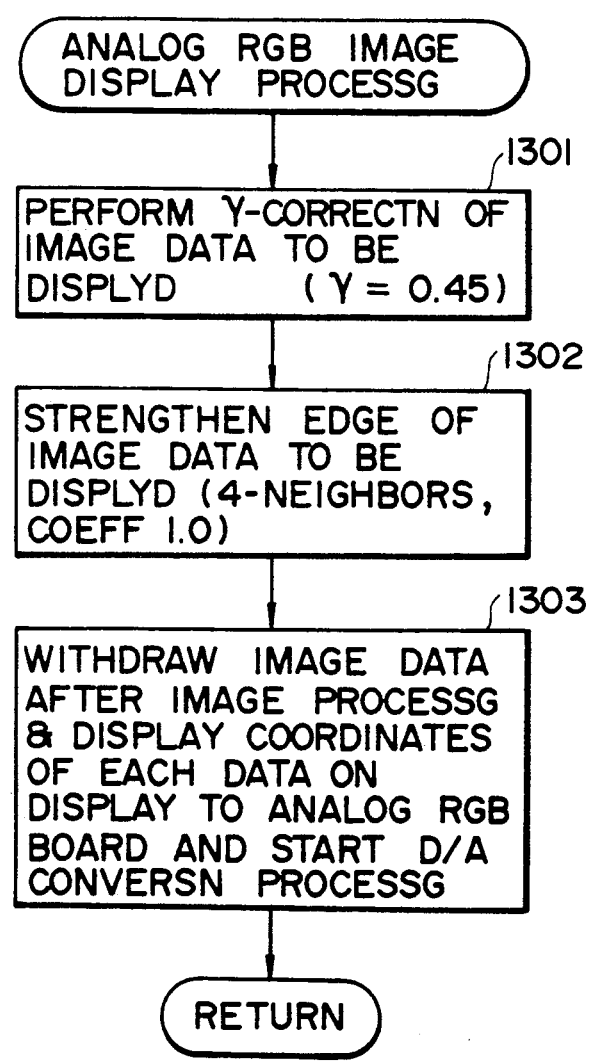
FIG. 13 is a flow chart showing a procedure of analog RGB image display processing in the image recognition and edit processing unit.

FIG. 13 is a flow chart showing the procedure of the analog RGB image display processing routine 309. As shown in FIG. 13, the analog RGB image display processing routine is implemented in such a manner as will be described hereinafter. At step 1301, a concentration of each pixel of the image data as a display object is subjected to gamma ($\gamma$) correction ($\gamma = 0.45$) in order to make a screen display with a high resolution. At step 1302, edges of the image data directed to a display object are strengthened (four neighbors, coefficient, 1.0). Then at step 1303, image data after image processing and data of display coordinates of data on the display screen are fed to an analog RGB output board 312, and the digital-analog (D/A) conversion processing i the analog RGB output board 312 is started, and the analog RGB image display processing is then returned.

Figure 14:
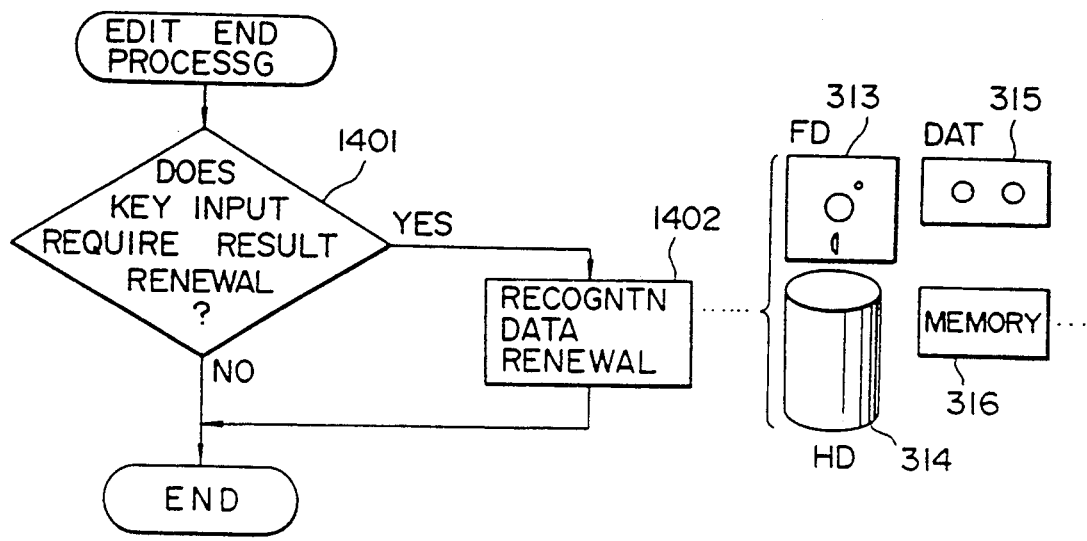
FIG. 14 is a flow chart showing a procedure of edit end processing in the image recognition and edit processing unit.

FIG. 14 is a flow, chart showing the procedure of the edit end processing routine 310. In the edit end processing routine as shown in FIG. 14, at step 1401, it is judged whether or not the key input is for a result renewal request. If YES, the flow goes to step 1402 where the content (FIG. 7B) of the recognition data of the DNA sequence as a result of edit processing is updated, thereby updating the recognition data of the DNA sequence stored in the floppy disk (FD) 313, the hard disk (HD) 314, the memory 316, digital-audio tape device (DAT) 315, or the like. If NO, the edit processing is suspended and no recognition data is updated.

Figure 15:
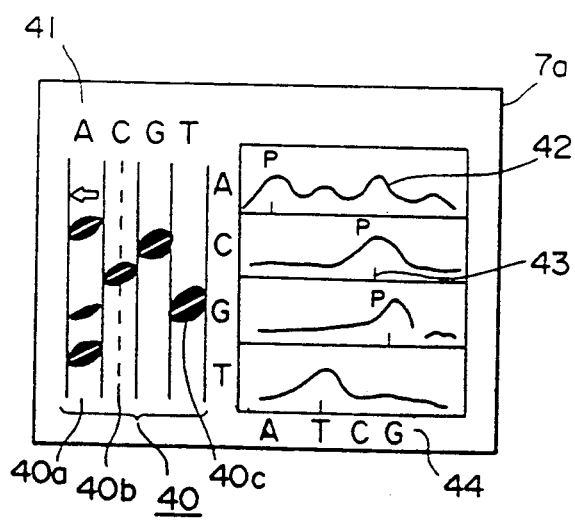
FIG. 15 represents one example of an edit screen of a DNA sequence on a display screen of the DNA pattern reader.

FIG. 15 represents one example of an editing screen of the DNA sequence on the display screen of the DNA pattern reading apparatus. In FIG. 15, reference numeral 7a denotes a display screen of the display unit. In editing the DNA sequence, a DNA film image 40 indicative of a band of the DNA pattern image of the DNA film is displayed on the left-hand side of the display screen 7a, together with a display 41 of each base of the DNA sequence, and a concentration graph of bands of each lane corresponding to each of the base displays 41 of the DNA sequence is displayed on the right-hand side thereof. The concentration graph 42 is a graph displaying concentrations of the band 40c in the center line 40b of each of the lanes 40a in the display DNA film image 40. A line 43 is displayed at a correct band position corresponding to a peak value in the concentration graph 2, together with a text 44 of the DNA sequence as a judgment result of the DNA sequence. To the judged band 40c, the marking display 40d indicating to have already been judged is added.

The edit processing of the DNA sequence is implemented in the manner as has been described hereinabove, while the DNA pattern image is simultaneously displayed on the screen. It is necessary, however, to add or delete the marking of the band which has already been judged, at a point as accurate as possible on the display screen of the DNA pattern image of the DNA film. Otherwise, there is the possibility that overlapping bands (overlapping the normalized positions) which should not originally appear would appear at a place where an interval between the bands is narrow, upon an addition of the band. It is preferred that the addition of the band be implemented at a position at which the concentration is thickest on the image display, however, it is difficult to visually give a position of the concentration peak of a band which is dark to some extent in concentration in a wide range.

Accordingly, the DNA pattern reading apparatus according to the present invention permits editing the DNA sequence, as shown in FIG. 15, by displaying the DNA pattern image 40 and, as required, by simultaneously displaying a concentration distribution of the DNA pattern image by a concentration graph 42. An addition of a judgment by the concentration graph 42 makes determination of a correct band position easy, and confirmation and correction of a result can be executed rapidly. In other words, as shown in an example of a display screen of FIG. 15, while the image data of the DNA pattern in the DNA film is displayed on the screen 7a of the analog RGB display, the concentration of the DNA sequence of the DNA film image 40 on each of the lanes is displayed by the concentration graph 42, whereby a difference of concentrations can be converted into a deviation of spaced coordinate positions so that a peak position P, i.e., a correct position, can be determined easily, thereby rapidly implementing a confirmation, correction or other acts of an accurate result.

Figure 16B:
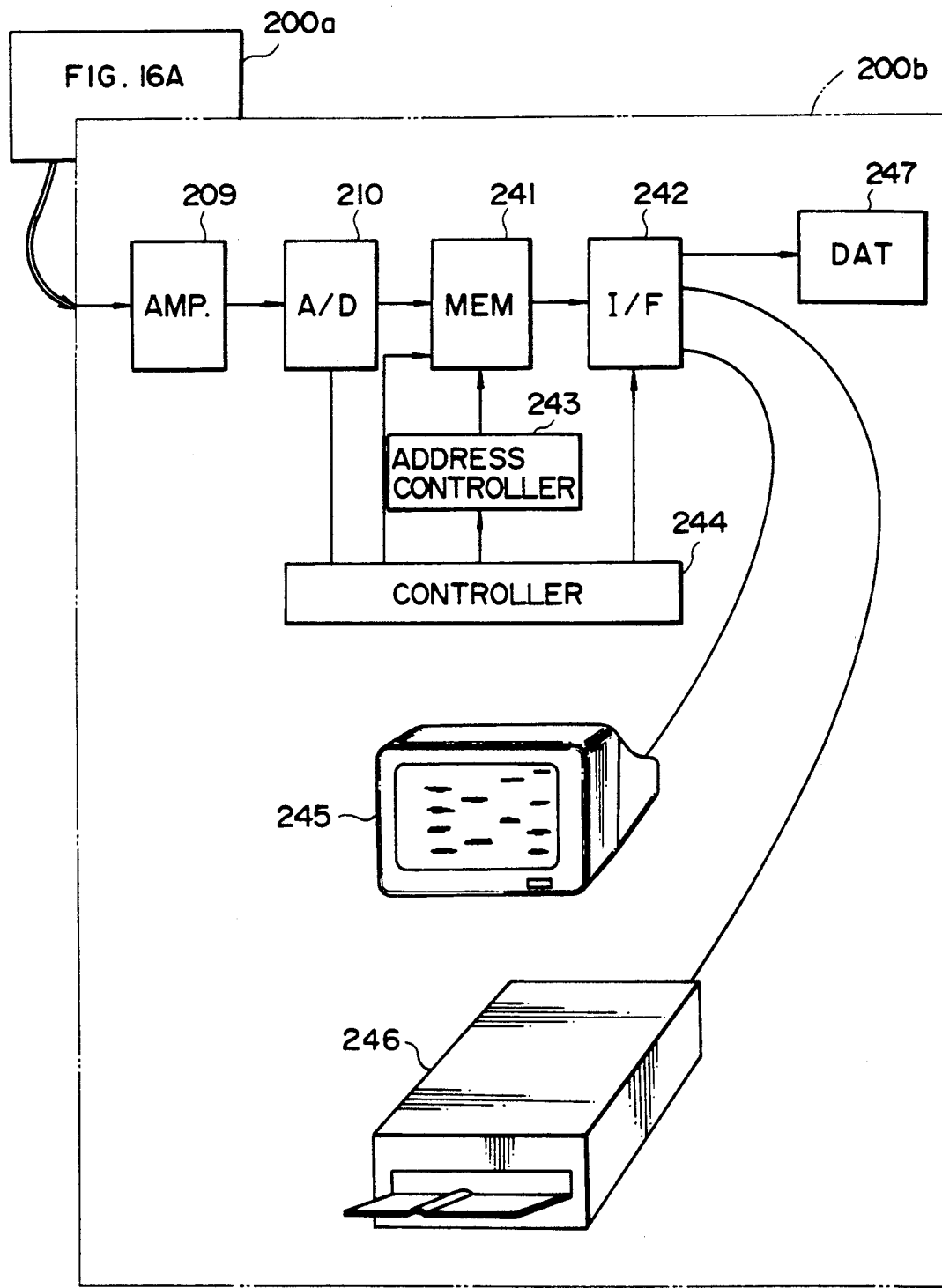

FIGS. 16A and 16B are block diagrams each showing a brief structure of a fluorescence detecting type electrophoresis system constructed according to the present invention, and capable of directly obtaining the DNA pattern., image. The fluorescence detecting type electrophoresis system comprises an electrophoresis device 200a as shown in FIG. 16A and a recorder unit 200b of the DNA pattern image as shown in FIG. 16B.

As shown in FIG. 16A, the electrophoresis device 200a comprises a light source 201 for activating fluorescence, an optical fiber 202 leading light from the light source 201, an electrophoresis unit 203 for carrying out electrophoresis, upper and lower electrodes 204 for applying voltage to the electrophoresis unit 203, an electric source 205 for applying voltage to the electrodes 204, a lens system 206 for receiving fluorescence, an optical amplifier 207 for amplifying an optical signal, and a one-dimensional optical sensor 208 for converting an image optically amplified by the optical amplifier 207 into electric signals.

As shown in FIG. 16B, the recorder unit 200b of the DNA pattern image comprises an amplifier 209 for amplifying an electric signal outputted from the one-dimensional optical sensor 208 of the electrophoresis device 200a, an analog-digital (A/D) converter 210 for digitizing the electric signal from the amplifier 209, a memory 241 for storing data obtained by the analog-digital (A/D) converter 210, an interface portion 242 for connecting the memory 241 to an output device, an address control circuit 243 for specifying an address for writing data in the memory 241, a control unit 244 for implementing an overall control, a display 245 for displaying the image, a film printer 246 for storage as a film, and so on.

Operation of the fluorescence detecting type electrophoresis will be described. As shown in the plan view of FIG. 17A and in the side view of FIG. 17B, the electrophoresis unit 203 has a structure in which gel 222 such as polyacrylic amide or the like is interposed between a pair of glass substrates 221. The gel 222 of the electrophoresis unit 203 is irradiated with the light from the light source 201 through the optical fiber 202 so as to form an optical path 213 from the lower left side of the electrophoresis unit 203. A fluorescent substance present in the optical path 213 in the gel 222 emits an activated fluorescence 24. The fluorescence 224 reaches the lens system 206 (FIG. 16A) and focuses at the optical amplifier 207 which amplifies an optical intensity to from several thousands to several tens of thousands of times. The amplified light reaches the one-dimensional optical sensor 208, converting into an electrical signal.

The electrical signal obtained by the one-dimensional optical sensor 208 is amplified by the amplifier 209 of the recorder unit 200b of FIG. 16B to an appropriate level and fed to the analog-digital converter 210. A quantum number in this example is 8 bits, for example. The timing of digitizing is given by the control unit 244, and a timing signal is added to the address control circuit 243 to synchronize the address formed by the address control circuit 243 with the writing of data. The digital-image data obtained in the manner described hereinabove is stored in time series in the memory 241.

Figure 18:
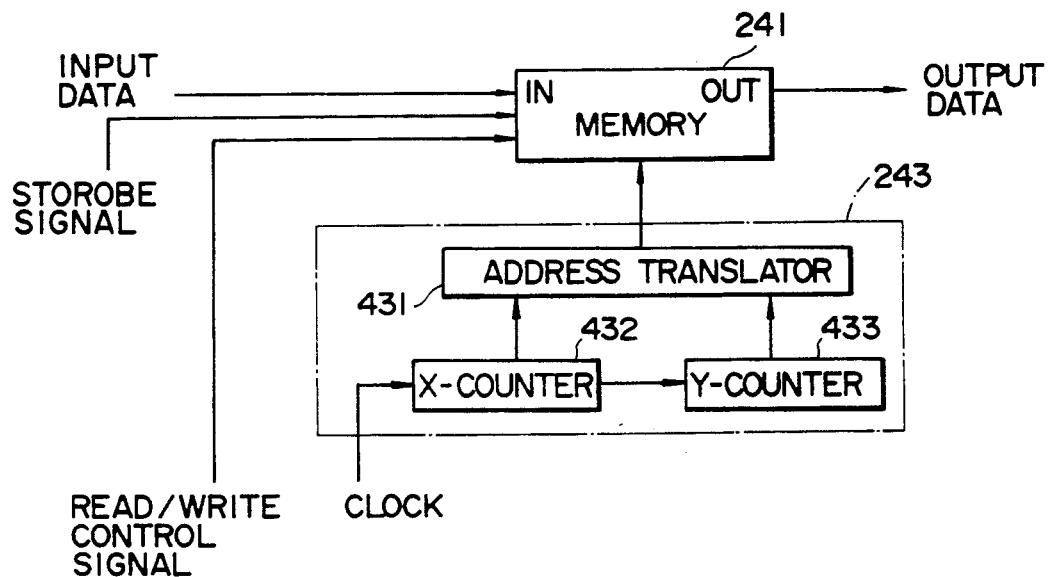
FIG. 18 is a block diagram showing the structures of a memory and an address control circuit, as shown in FIG. 16B.

The structure of an essential portion of the memory 241 and the address control circuit 243 will be shown in FIG. 18. As shown in FIG. 18, the address control circuit 243 comprises an address converting circuit 431, an X counter 432, and a Y counter 433.

The X counter 432 is a counter which repetitively counts, for example, 2,376 counts from "0" to "2,375". As the count number is 2,375, a carry (a carry signal) generates. This carry is added to the Y counter 433 and the Y counter 433 is increased by one increment. The address converting circuit 431 is to convert an address for using the memory 241 effectively. As a capacity of the memory 241 is 2 to the N-th power wherein N is a number of address inputs, the address is from "0" to "$2^N - 1$". In this example, the data number in the x-direction is 2,376 so that addresses of at least 12 bits are required $(2^{11} = 2,048 < 2,376 < 2^{12} = 4,096)$. Accordingly, an output of the Y counter 433 as an upper address and an output of the X counter 432 as a lower address is added to the addressing of memory, so that addresses from "2,376" to "4,095" for each y address value are not used. This worsens a use efficiency of the memory 241. In order to avoid this, the following conversion is carried out in the address converting circuit 431:

*Memory address* $= y \times 2{,}376 + x$

In order to compute the above conversion, an adder and a multiplier are basically required.

In this example, the multiplication on the first part in the formula above is computed in advance and written in ROM (Read Only Memory), RAM (Random Access Memory) having addresses of the maximum value, or the like. Accordingly, the multiplication is merely a ROM access, making a circuit simple, less expensive, and of a high speed. This also can deal with an alteration in a number of pixels in the x-direction. The address control circuit may be constituted, for example, by an adder for adding an output of the ROM and the X counter.

Figure 19:
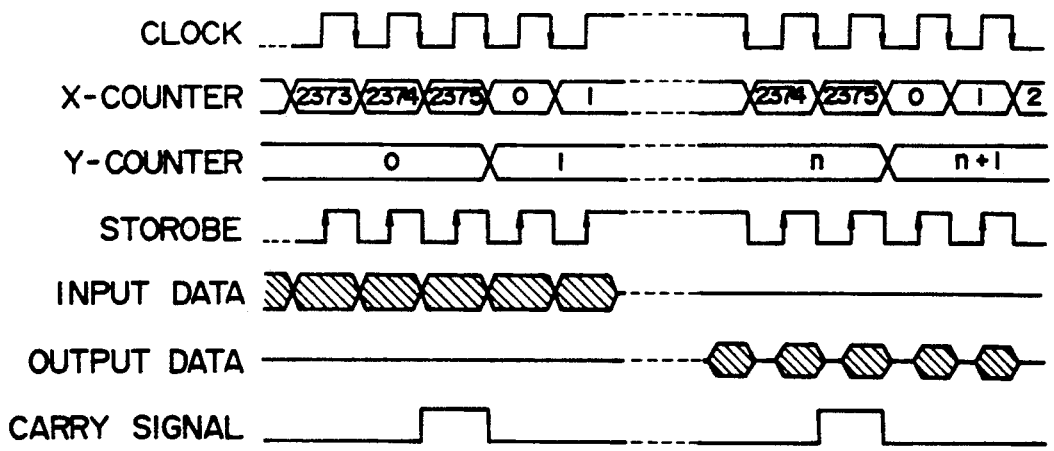
FIG. 19 is a timing chart for explaining a recording operation by the memory and the address control circuit, as shown in FIG. 16B.

These operations will be described using a timing chart shown in FIG. 19. The case of writing an output from the analog-digital converter 210 into the memory 241 will be first described. Referring to the left-hand side of FIG. 19, the X counter 432 is increased at the rise of a clock coming from the control unit 244. As the count value of the X counter reaches 2,375, a carry is outputted as shown in the drawing to increase one count. Data (shaded with oblique lines) from the analog-digital converter 210 is outputted to a data line in synchronization with the rise of the clock, thus writing in the memory 241 at the rise of a strobe signal in which addresses and data are stable.

Figure 17A:
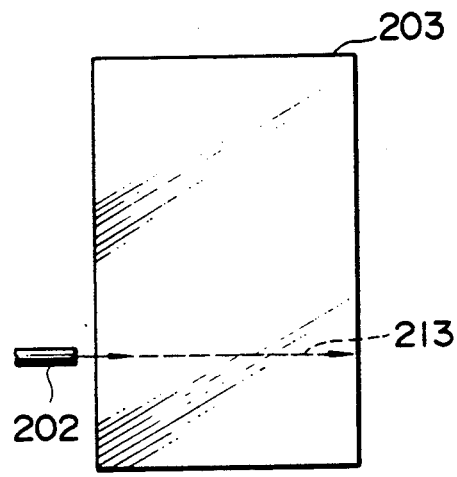
FIG. 17 is a diagram for explaining the structure of an electrophoresis portion of FIG. 16A.
Figure 17B:
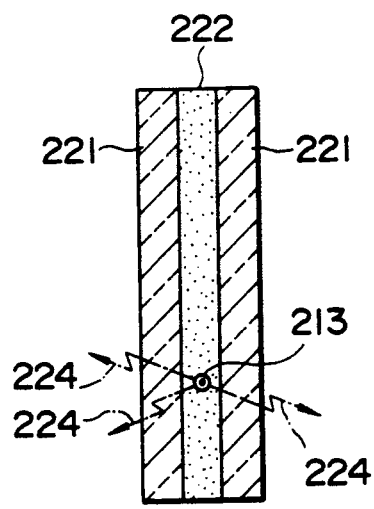
Figure 20:
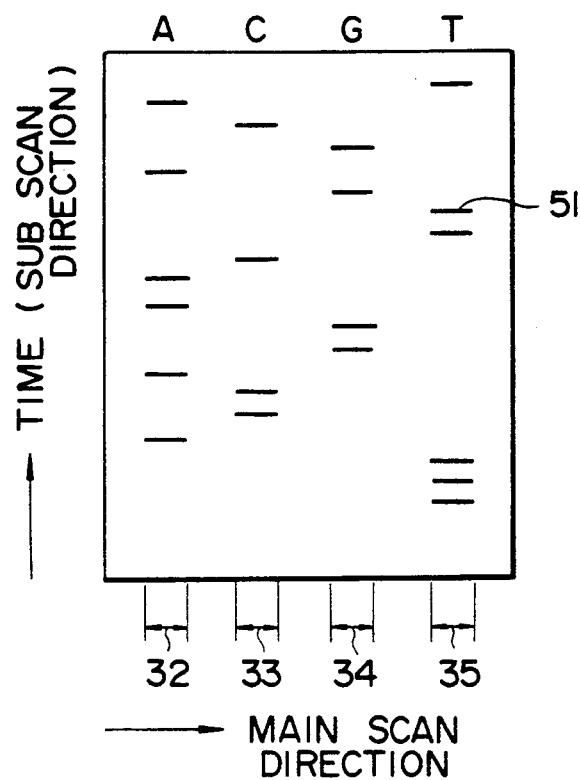
FIGS. 20, 21A and 21B are diagrams showing electrophoresis patterns of DNA.
Figure 21A:
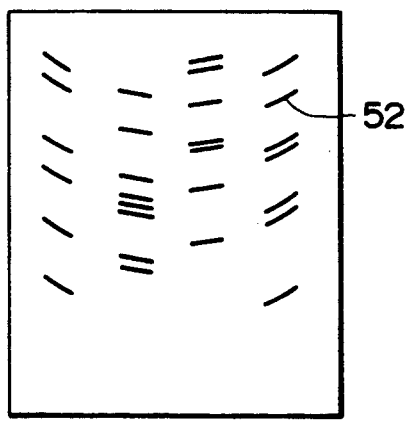
Figure 21B:
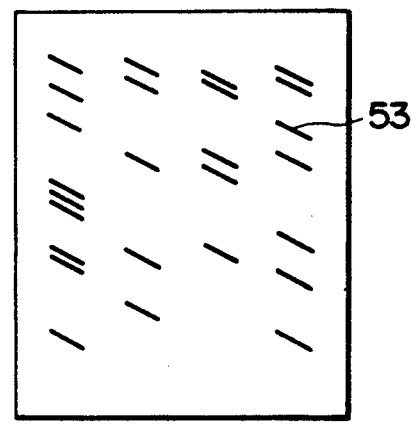
Figure 22:
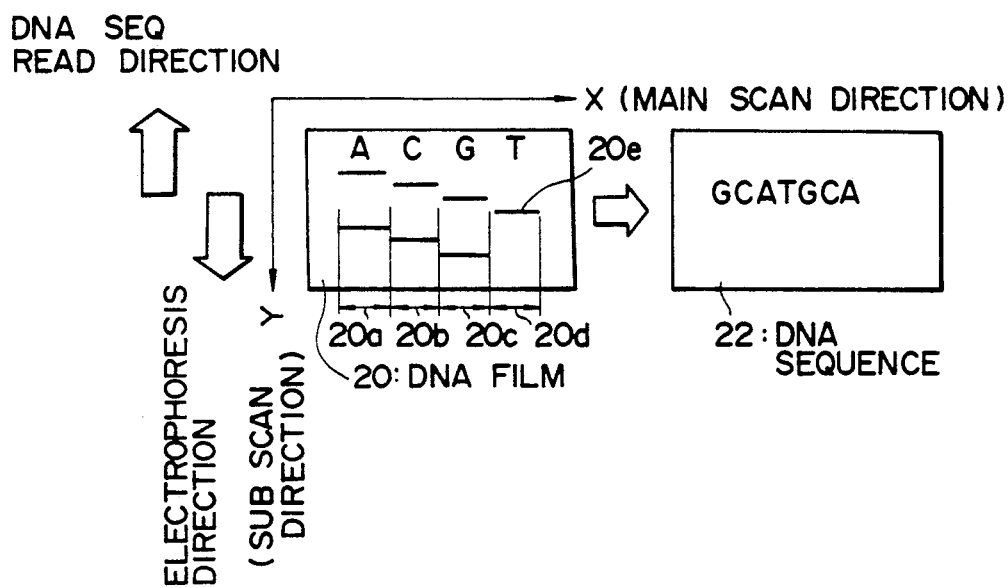
FIGS. 22 and 23 are diagrams for explaining an outline of the DNA pattern reading apparatus.
Figure 23:
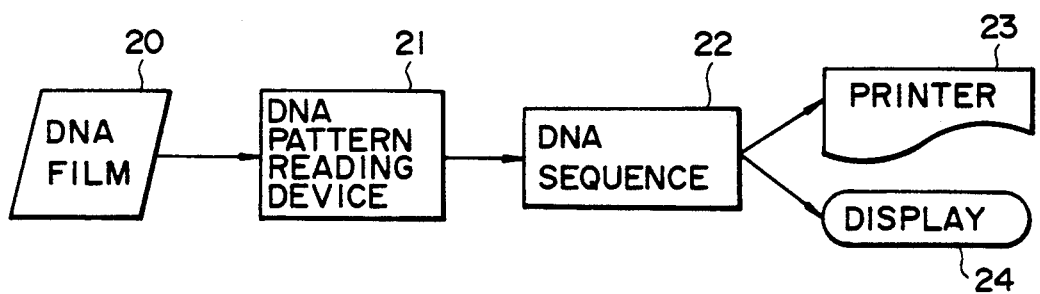

Referring now to the right-hand side of FIG. 19, a description will be made of the case of reading data from the memory 241 to output data or the like. As shown in the drawing, a timing of this read operation generates a read address by adding a clock in the same manner as in the write operation. As the strobe signal becomes true (a high level), data is outputted during that period of time and the output is fed to the interface portion 242. The interface portion 242 is provided with an analog-digital conversion function as well as a function of outputting digital data from the memory as it is. The functions enable an output of the data to the digital-audio tape recorder 247 as it is and an output of a video signal converted into an analog signal to the display 245 on the basis of an instruction from the control unit 244. They can also output, for example, to the film printer 246 of an optical type, as needed. As an output result, an electrophoresis pattern image of a DNA may be obtained as shown in FIGS. 20, 21A, and 21B. In the DNA pattern image, the abscissa is a main scan direction, on the one hand, and it indicates a direction in which the one-dimensional image sensor is disposed along the optical path 213 (in the main scan direction), for example, as shown in FIG. 17A. The ordinate corresponds to a direction in which a time elapses. The bands 51 corresponding to the position of the DNA fragment are disposed in such a manner that the minimum pitch of the ordinate is in approximately equal intervals as a whole. This is because of a distribution of fluorescence during a passage through the position of the optical path 213 (FIG. 17) in contrast to an image of an overall electrophoresis surface during the electrophoresis. In FIG. 20, reference numerals 32 to 35 stand for positions corresponding to each of the lanes of the DNA to be subjected to electrophoresis. As shown in FIGS. 21A and 21B, a distribution pattern of the DNA segment obtained by the electrophoresis may be shown to be curved like bands 52 (referred to as "smiling") or inclined like bands 53. These phenomena may be caused because of fluctuations in a distribution of temperatures created during electrophoresis or in a gel state or for other various reasons. In these cases, the present invention permits a provision of an accurate DNA sequence by recording an electrical signal of a distribution pattern of the DNA segment subjected to electrophoresis, obtaining the DNA pattern image, judging the DNA sequence and thereafter editing the DNA sequence.

As has been described hereinabove, the fluorescence detecting type electrophoresis to be used for the present invention can read a distribution of fluorescence directly from the gel subjected to electrophoresis and store the DNA pattern in the memory, so that the DNA pattern image can be obtained without forming any DNA film.

The present invention has been described specifically by way of examples, but it is to be understood that the present invention should be interpreted to be not restrictive to those examples and to encompass various modifications and changes without departing from the spirit and scope of the present invention.

The present invention permits a reproduction of the DNA pattern image data of the DNA film, a rapid confirmation of an accurate result and a rapid correction of editing of the DNA pattern image by displaying the concentration graph of each lane in the DNA film image and editing the DNA sequence. As a result, laborious work such as a visual proof-reading of the DNA film upon confirmation of the result, which is essential for the conventional DNA pattern reading apparatus, is not required any more, thereby reducing the burden of labor to a considerably large extent and improving an accuracy of editing the read result. The DNA pattern reading apparatus according to the present invention further does not require a file of the read DNA pattern image data to be taken from a storage, thereby preventing the DNA film from being damaged or deteriorated.

What is claimed is:

1. A DNA pattern reading apparatus for reading a DNA pattern image resulting from electrophoresis of a labeled DNA fragment of a gene and automatically determining a base sequence of the gene, comprising:
   image storage means for storing a DNA pattern image;
   image recognition and edit processing means for reading the stored DNA pattern image from the image storage means, processing the DNA pattern image and an image of the DNA sequence derived from the stored and read DNA pattern image, and for editing the DNA sequence in accordance with the stored and read DNA pattern image, including band deletion processing means and band addition processing means for correcting the DNA pattern image; and
   display means for displaying the DNA pattern image together with the edited DNA sequence.

2. A DNA pattern reading apparatus as claimed in claim 1, wherein said image recognition and edit processing means comprises:
   data processing means for judging the stored and read DNA pattern image, for judging the DNA sequence derived from the stored and read DNA pattern image, for outputting data representing the judged DNA sequence for display, for outputting data representing the judged DNA pattern image for display, for image processing the stored and read DNA pattern image and the DNA sequence, and for edit processing the DNA sequence in accordance with the stored and read DNA pattern image.

3. A DNA pattern reading apparatus for reading a DNA pattern image resulting from electrophoresis of a labeled DNA fragment of a gene and automatically determining a base sequence of the gene, comprising:
   image storage means for storing a DNA pattern image;
   image recognition and edit processing means for judging, in a multi-portion process, the DNA sequence derived from the DNA pattern image, for outputting the DNA sequence as a result of said multi-portion judgment, for outputting the judged DNA pattern image and an image of each portion of the multi-portion judging process corresponding to a display portion of the DNA sequence as a result of said judgment, for image processing the DNA pattern image and the DNA sequence, and for edit processing the DNA sequence in accordance with the stored and read DNA pattern image, including band deletion processing means and band addition processing means for correcting the DNA pattern image; and
   display means for displaying the DNA pattern image together with the edited DNA sequence.

4. A DNA pattern reading apparatus as claimed in claim 3, wherein the image recognition and edit processing means further comprises:
   concentration graph display processing means for producing a concentration graph indicative of a distribution of concentrations in a selected one of a main scan direction and a sub scan direction of a DNA pattern image, and for outputting a concentration graph;
   smiling cursor display processing means for forming a reference line for correcting a distortion of the DNA pattern image; and
   cursor transfer processing means and display screen scroll processing means for enabling modification of the displayed DNA pattern image and DNA sequence;
   wherein the DNA pattern image and the DNA sequence are image processed before the DNA sequence is edit processed.

5. A DNA pattern reading method, comprising:
   storing image data of a DNA pattern image in an image storage;
   determining the DNA sequence of the DNA patter image;
   judging the DNA sequence for errors;
   converting the DNA sequence into data representing the DNA sequence;
   simultaneously displaying the DNA sequence and the DNA pattern image along with a textual representation of the DNA sequence; and
   editing the DNA sequence by correcting distortion of the DNA pattern image by comparison to a reference line, and by selectively subjecting the corrected DNA sequence and the corrected DNA pattern image to band deletion processing and band addition processing.

6. A DNA pattern reading method as claimed in claim 5, wherein the editing of the DNA sequence comprises the steps of:
   displaying a concentration graph indicative of a distribution of concentration in a selected one of a main scan direction and a sub scan direction of reading the DNA pattern image;

displaying the reference line;

confirming and correcting the DNA pattern image and the DNA sequence; and displaying and confirming the DNA pattern image.

7. A DNA pattern reading method as claimed in claim 6, wherein the editing of the DNA sequence further comprises the steps of:

specifying a screen position to be edited using a displayed cursor; and scrolling the displayed image in order to display a portion of the DNA pattern image that is not currently displayed.

8. A DNA pattern reading method as claimed in claim 6, wherein the editing of the DNA sequence further comprises the steps of:

executing an image display of DNA pattern image data and the concentration graph on a display screen;

executing a line display indicative of each of a plurality of judged bands of the DNA pattern image so as to overlap with the image display of the DNA pattern image data and the concentration graph;

judging and editing the DNA sequence;

displaying textually the DNA sequence data;

selectively deleting or adding data of the DNA sequence from or to a band position in the DNA pattern image when an error in judging the DNA sequence has occurred;

image processing the DNA pattern image and the DNA sequence; and editing the DNA sequence.

* * * * *